(12) United States Patent
Link

(10) Patent No.: US 7,896,903 B2
(45) Date of Patent: Mar. 1, 2011

(54) FACET JOINT PROSTHESIS

(75) Inventor: Helmut D. Link, Hamburg (DE)

(73) Assignee: DERU GmbH, Norderstedt (DE)

( * ) Notice: Subject to any disclaimer, the term of this patent is extended or adjusted under 35 U.S.C. 154(b) by 1051 days.

(21) Appl. No.: 11/637,237

(22) Filed: Dec. 12, 2006

(65) Prior Publication Data

US 2007/0149983 A1  Jun. 28, 2007

Related U.S. Application Data

(60) Provisional application No. 60/749,588, filed on Dec. 13, 2005.

(51) Int. Cl.
*A61B 17/70* (2006.01)
*A61F 2/44* (2006.01)

(52) U.S. Cl. ...................... 606/247; 623/17.11

(58) Field of Classification Search ............... 623/17.11; 606/247

See application file for complete search history.

(56) References Cited

U.S. PATENT DOCUMENTS

| | | | | |
|---|---|---|---|---|
| 5,119,805 | A * | 6/1992 | Cadoret | 602/16 |
| RE36,758 | E | 6/2000 | Fitz | |
| 7,588,590 | B2 * | 9/2009 | Chervitz et al. | 606/247 |
| 7,591,851 | B2 * | 9/2009 | Winslow et al. | 623/17.11 |
| 7,601,171 | B2 * | 10/2009 | Ainsworth et al. | 623/17.11 |
| 7,608,104 | B2 * | 10/2009 | Yuan et al. | 623/17.11 |
| 2003/0004572 | A1 | 1/2003 | Goble et al. | |
| 2004/0049272 | A1 | 3/2004 | Reiley | |
| 2005/0049705 | A1 | 3/2005 | Hale et al. | |
| 2005/0055096 | A1 * | 3/2005 | Serhan et al. | 623/17.11 |
| 2005/0119748 | A1 | 6/2005 | Reiley et al. | |
| 2005/0159746 | A1 | 7/2005 | Grob et al. | |
| 2005/0177240 | A1 * | 8/2005 | Blain | 623/17.15 |
| 2005/0261770 | A1 * | 11/2005 | Kuiper et al. | 623/17.11 |
| 2006/0036246 | A1 * | 2/2006 | Carl et al. | 606/61 |
| 2006/0036259 | A1 * | 2/2006 | Carl et al. | 606/90 |
| 2007/0088358 | A1 * | 4/2007 | Yuan et al. | 606/61 |

FOREIGN PATENT DOCUMENTS

| | | |
|---|---|---|
| WO | WO-2004/098465 | 11/2004 |
| WO | WO-2004/103227 | 12/2004 |
| WO | WO-2005/037149 | 4/2005 |
| WO | WO-2006/065774 | 6/2006 |

OTHER PUBLICATIONS

International Search Report dated Feb. 20, 2007, directed to counterpart international application No. PCT/EP2006/012007.

* cited by examiner

*Primary Examiner* — Eduardo C Robert
*Assistant Examiner* — Ellen C Hammond
(74) *Attorney, Agent, or Firm* — Morrison & Foerster LLP

(57) ABSTRACT

A prosthesis for facet joints of the spinal column includes a bearing piece and a guide rod. The bearing piece includes a pressure plate that is configured for resting on an articular surface of the vertebra and, on the opposite side, a bearing insert which has an articular surface configured for interacting with an articular surface of an adjacent vertebra. The guide rod is secured on the bearing piece by means of a pivot joint. The bearing forces are transmitted to the vertebra via the pressure plate. In this way, the guide rod can have a narrow configuration, such that a slit excavated in the vertebra for receiving the guide rod can also be made narrow to permit a simple and reliable implantation technique which at the same time is gentle on the bone substance.

23 Claims, 2 Drawing Sheets

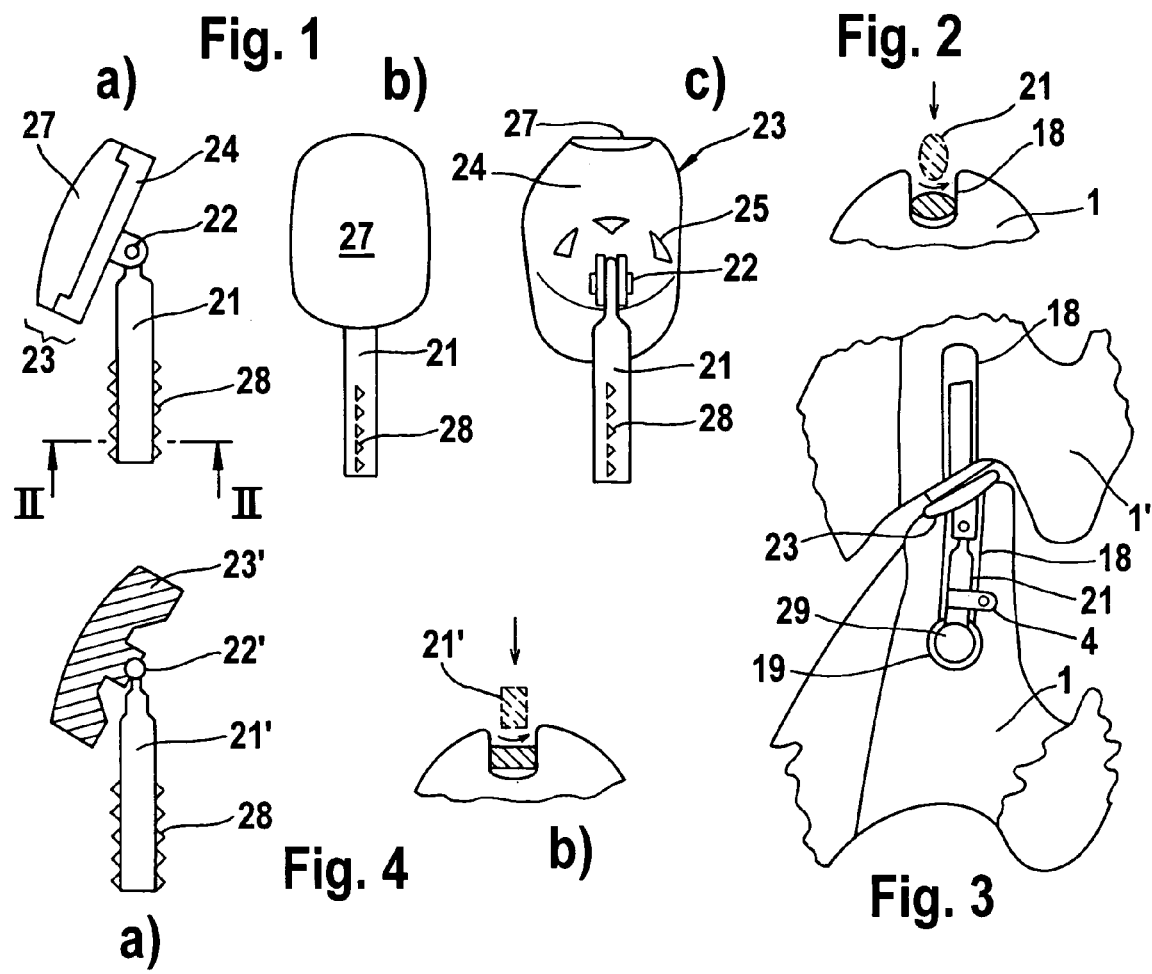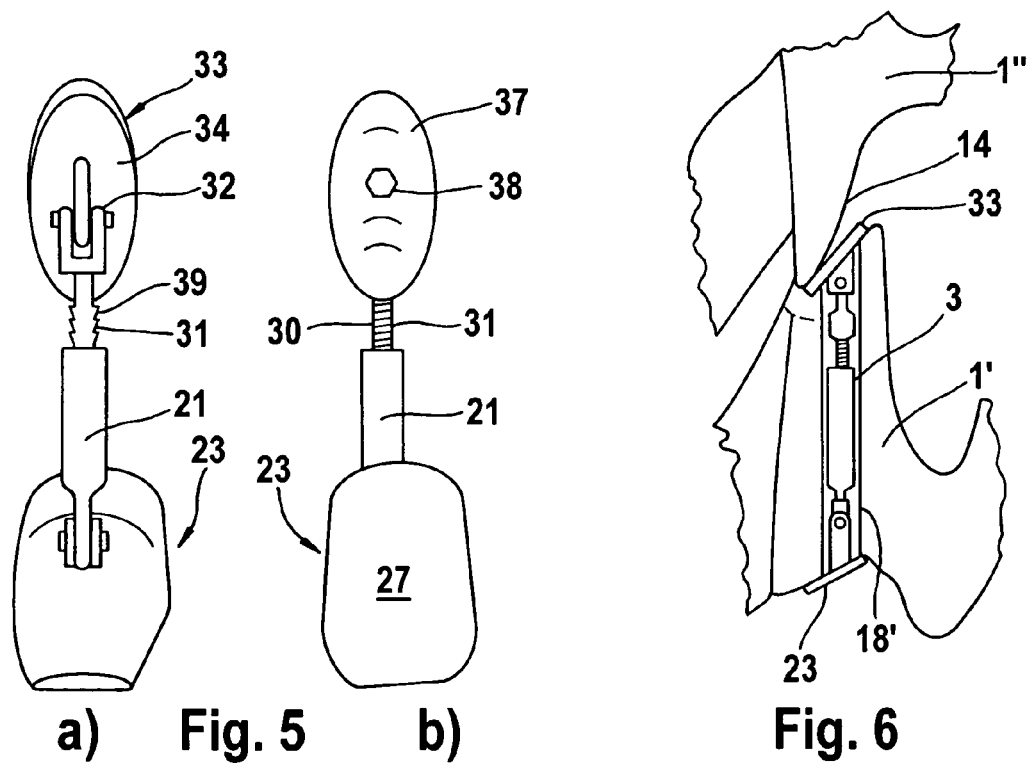

FACET JOINT PROSTHESIS

REFERENCE TO RELATED APPLICATION

This application claims priority from U.S. Provisional Application No. 60/749,588, filed Dec. 13, 2005, the entire contents of which are incorporated herein by reference.

FIELD OF THE INVENTION

The invention relates to a prosthesis for facet joints of the spinal column, with a bearing piece and a retaining piece.

BACKGROUND OF THE INVENTION

Back problems can often be attributed to pathological changes in the area of the spinal column. One of the main causes lies in the interaction between two adjacent vertebrae and their connection. This in particular concerns intervertebral disks and facet joints. The connection between vertebrae may become damaged because of disease or overloading, either through injury or wear. This can lead to restricted movement, pain, or even loss of mobility. In the past, therapy was focussed on treating the intervertebral disks. Thus, various artificial joints were proposed which are implanted in place of a defective natural intervertebral disk. In this way, defects on the facet joints could also be indirectly compensated, and their consequences alleviated. However, it has been shown that this is not sufficient and that, in many cases, targeted therapy of the facet joints is also needed.

Various approaches have been attempted for treatment in the area of the facet joints. In the simplest case, treatment is restricted to reducing the pain caused by the facet joint, in particular by injection of analgesics in the area of the affected facet joint. A further possibility is that of removing the facet joint. This of course eliminates one of the causes of pain, but at the price of a significant change to the biomechanics of the spinal column. The absence of facet joints reduces the stability of the spinal column to a great extent and thus leads to greater loading of the other areas of the spinal column, which often leads to defects in the area of adjacent connection between vertebrae. The same applies to the reverse approach, namely that of immobilizing the facet joint by a fixed connection. Here too, the biomechanics are negatively affected. The mobility of the patient deteriorates, and there is greater loading in the area of the adjacent vertebrae.

It has also become known to provide the facet joints with a protective cap in the area of their articular surface. To create space for the cap, a considerable amount of material has to be removed from the natural bearing surface. This removal of tissue often leads to an interruption of the natural supply of surrounding healthy tissue, with the consequence of necrotic changes.

To avoid said disadvantages of these traditional treatment methods, various prostheses for facet joints have been developed.

A complicated intervertebral disk prosthesis, with additional facet joint prostheses that can be attached thereon, is known from WO-A-2004/098465. The prosthesis is thus suitable for simultaneous treatment of the intervertebral disk and of the facet joints. As a result of this combination, the prosthesis has a complicated structure and has relatively large dimensions. This necessitates a complex operation with an access route of large dimension. Treatment of the facet joints in the area of the cervical spine is difficult with this prosthesis.

A more compact prosthesis for a facet joint is known from WO-A-2005/037149. It comprises an elastic element with a disk-shaped thickening which is placed between the bearing surfaces of the facet joint. The prosthesis is secured by fastening elements that are introduced into through-holes in the corresponding articular processes. Since these through-holes have to be flush with one another, their creation is very difficult and requires an unimpeded access. The prosthesis further creates a flexible mechanical tensile connection of the facet joint, of a type that was not originally present.

Another special facet joint prosthesis is known from WO-A-2004/103227. It consists of two components which each have a bearing piece and a retaining piece for anchoring on the adjacent vertebrae. An upper component is anchored in the lamina of the vertebra by means of a screw. The screw has a relatively long shaft, which leads to unfavorable lever ratios and thus to a loading of the lamina. To avoid buckling of the screw, it has to have relatively large dimensions. The prosthesis comprises many protruding parts, which poses a danger of irritation of surrounding tissue. In addition, the fastening of the upper bearing component on the lamina instead of on the corresponding articular process changes the biomechanics. A similar facet joint prosthesis with a translaminar fastening screw is known from US-A-2005/0049705. The fastening screw lies with its head on the lamina and extends through a channel created in the vertebra to the lower facet joint surface, where a bearing piece is arranged and fixed by means of the fastening screw. The bearing piece interacts with a mating piece of the facet joint, which mating piece is arranged on the adjacent vertebra and is secured on the vertebra by means of a simple spike. A disadvantage of this prosthesis is that creating the translaminar channel is quite complicated, and a pass-fit joining of bearing piece and screw is difficult, since it depends on the particular angle of the facet joint surface. Considerable maneuvering difficulties arise particularly in the cervical area of the spinal column.

US-A-2004/0049272 discloses a facet joint prosthesis which comprises a bearing piece with a retaining rod rigidly mounted thereon and protruding into the vertebra. The bearing piece has a cup-shaped curvature and comprises a pressure plate for resting on the vertebra, and a bearing shell which interacts with a felt-type mating piece on the corresponding opposite face of the facet joint. The retaining rod can be connected permanently or releasably to the bearing piece. However, this prosthesis too is difficult to maneuver, especially in confined spatial conditions, such as those in the cervical spine area, if the retaining rod and mating piece have to be joined together in situ. If they are pre-assembled, then there is the difficulty of introducing them under the confined spatial conditions. For secure fixing, the retaining rod has to protrude far into the area of the vertebral body, which can lead to irritation there.

U.S. Pat. No. 177,240 discloses a facet joint prosthesis which comprises a bearing piece with a guide rod that can be screwed thereon. The bearing piece is designed, on its underside, as a pressure plate for resting on the vertebra, and, on its opposite side, as a bearing surface for interaction with a mating articular surface. At its opposite end, the guide rod has a mating element which can be provided with a screwdriver receiver. The guide rod is secured on the bearing piece by means of a screw connection. Under confined conditions, especially in the area of the cervical spine, creating a corresponding through-bore at an exact position, and connecting the bearing piece to the guide rod, can cause considerable difficulties.

SUMMARY OF THE INVENTION

The object of the invention is to create an improved prosthesis for facet joints which is less invasive and has biomechanics more closely approximating to the natural facet joint.

The solution according to the invention lies in the features of the invention as broadly disclosed herein. Advantageous developments are the subject matter of the preferred embodiments.

In a prosthesis for facet joints of the spinal column with a bearing piece and a guide rod as retaining piece, whose bearing piece comprises a pressure plate for resting on the vertebra and, on the opposite side, a bearing shell which has an articular surface for interacting with an articular surface of an adjacent vertebra, a pivot joint is provided according to the invention for securing the guide rod on the bearing piece. The core of the invention is the concept of creating a prosthesis in which, on the one hand, the function of retaining the prosthesis at its intended site is detached from the function of taking up the bearing forces, and which, on the other hand, can be adapted to different anatomical conditions and can thus be easily fitted. The articular surfaces of the facet joints are formed at different inclinations on the vertebrae. Thoracic vertebrae have a different inclination than cervical vertebrae. To be able to easily compensate for these differences, and also for individual differences between different patients, the guide rod is secured on the bearing piece via a pivot joint. This allows the angle to be adapted to the particular anatomical circumstances. The invention does not require a channel which is exactly oriented with respect to the bearing surface at a defined angle and into which a fastening screw has to be inserted and connected to the bearing piece, and instead the invention requires only a simple slit to be formed whose angular orientation with respect to the bearing surface can vary within wide limits. It facilitates the insertion of the prosthesis according to the invention in the correct position and permits a surgically favorable excavation of the slit on the vertebra, namely on the articular process in the direction between the upper and lower articular surfaces. The facet joint prosthesis according to the invention simply requires to be introduced into this slit, without the need for complicated assembling or connection of the various elements, and, in particular, in contrast to the prior art, the guide rod does not have to be connected to the bearing piece via a screw connection. The invention is therefore particularly suitable for implantation at spatially confined locations that are difficult to access, in particular in the area of the cervical spine. By virtue of the ease with which it is fitted in place, the prosthesis according to the invention can be made small. This makes it possible to manage with a small guide rod and, consequently, a small slit. The work needed for this on the vertebra is minimal. The slit can be worked from the side into the vertebra, preferably in the dorso-lateral direction. This prosthesis thus permits a particularly favorable access route. The prosthesis according to the invention permits substantial preservation of the natural substance. In this way, the prosthesis according to the invention is suitable for an operation that is only minimally invasive. The prosthesis according to the invention, with a suitably chosen curvature of the bearing surface, even permits partial replacement on one side, that is to say the interaction with the natural articular surface of the adjacent vertebra. In addition, the kinematic center of the articulation remains at its original site with the prosthesis according to the invention. Consequently, the prosthesis according to the invention combines favorable biomechanics with the advantages of comparatively easy implantation, which is also only minimally invasive.

For more precise adaptation to individually different anatomies, however, it can be advantageous if the pivot joint is movable in a second direction transverse to the longitudinal axis of the guide rod. A mobility in the frontal plane is thereby achieved. For this purpose, the pivot joint can be designed as a ball joint, or preferably as a cardan joint.

The guide rod is expediently arranged in its middle position on the bearing piece at an angle with respect to the pressure plate. An anatomically favorable form is thus achieved. In general, it suffices if the pivot joint is movable in a direction transverse to the longitudinal axis of the guide rod. A mobility in the sagittal plane is thereby achieved.

In the simplest case, the guide rod has a circular cross section. However, it is expedient if it has a non-circular, preferably rectangular or oval cross section. The dimensions are chosen such that the width of the guide rod, depending on its orientation, is smaller or greater than the width of the slit. This makes it possible to introduce the guide rod in its narrow orientation into the slit, and to turn it about its longitudinal axis, at its intended site, until it becomes wedged in the slit. It is thus protected against inadvertently slipping out. In the case of a rectangular cross section, the edges can provide a locking effect by which additional securing is obtained. However, the non-circular cross section is not absolutely essential since, by virtue of the possible small dimensioning of the slit according to the invention, the latter can generally be expected to close rapidly. To further protect the prosthesis according to the invention against undesired dislocation, a radially protruding serration can expediently be provided along the guide rod. It further secures the guide rod against undesired slipping to the sides. For this purpose, a bracket can also be provided on the guide rod and is used for fastening to the vertebra, for example by means of screwing.

To secure the bearing piece additionally on the vertebra, the pressure plate is expediently provided with a toothing arrangement designed to engage in the vertebra. The bearing piece thus presses automatically into the vertebra under the effect of the bearing forces. In this way, it is further protected against displacement or twisting. The toothing arrangement can consist of individual teeth, or one row of teeth can be provided, for example in a circular arrangement. To further improve the connection to the vertebra, a coating that promotes bone growth can additionally be provided on the pressure plate. One example of such a coating is hydroxyapatite. This promotes the incorporation of the prosthesis on the vertebrae.

The shell arranged on the opposite side of the bearing piece from the pressure plate preferably has a convex or concave curvature. The appropriate curvature will depend on the anatomical shape of the corresponding vertebra. It is expediently chosen such that it matches the shape of the articular surface which is arranged on the adjacent vertebra and with which the prosthesis forms the facet joint.

According to a particularly advantageous embodiment, which may deserve independent protection, a second bearing piece with pressure plate and bearing insert is arranged at the other end of the guide rod. A prosthesis can thus be formed with facet joints at adjacent levels can be treated. Only one slit is needed, into which the guide rod of the prosthesis is to be inserted. A further advantage of this embodiment is that the pressure plates arranged at both ends of the guide rod ensure additional securing. The guide rod is in this case preferably designed in several parts.

A telescopic configuration of the shaft is expedient. In this way, the length of the guide rod can be adapted to the thickness of the vertebra, more precisely to the length of the slit from one articular surface of the vertebra to the other. The telescope can be formed by elements running concentrically one within the other, or by a screw connection. To prevent undesired moving apart, which would entail a risk of loosening of the bearing pieces from their seat on the vertebrae, locking means are expediently provided for the shaft parts of the guide rod. For this purpose, special catch elements can be provided. However, the screw connection can also be chosen with a thread pitch that provides self-locking. The screw connection affords the advantage that, by simple turning of one of the bearing pieces, the length of the guide rod can be changed, so as to obtain a secure fit of the bearing pieces. For this purpose, a recess for a screw key is expediently provided on at least one of the bearing pieces.

The bearing pieces at the two ends of the guide rod can be differently configured. It is particularly expedient for a bearing piece at one (upper) end of the guide rod to have a contour with a circular envelope, and for the bearing piece at the other (lower) end to have a contour with a rectangular envelope. The terms circular and rectangular are not to be understood here in the strictly mathematical sense, but in the general sense. In particular, the rectangle can have rounded corners such that it has an oval-like shape. With this configuration, better approximation to the shape of the natural articular surfaces of the facet joints can be achieved.

However, it is not absolutely essential to arrange a second bearing piece on the opposite end of the guide rod. It is equally possible for a thickened part to be formed there. This thickened part expediently has a curvature on its side directed toward the bearing piece. In this way, the greater security of the fastening can be obtained when treating one joint, in the same way as with bearing pieces at both ends. The configuration as a thickened part permits a recessed arrangement in the vertebra, such that the guide rod with the thickened part does not protrude from the vertebral body, in contrast to cases with a second bearing piece. If the natural articular surface of the adjacent facet joint is worth preserving, it can in this way be retained, if appropriate. For implantation, the slit simply has to be widened at the site provided for receiving the thickened part, for example widened by drilling. A rotationally symmetrical design of the side of the thickened part facing the bearing piece is expedient, preferably as a curvature. In this way, when creating an additional receiving space by a drill, the thickened part can lie with particularly good contact on the bone substance, specifically also when the guide rod is turned about its longitudinal axis for fixation. A particularly expedient shape for a thickened part is a ball or a sphere.

The prosthesis according to the invention is suitable in particular for treatment at several adjacent levels of vertebrae. For this purpose, a prosthesis set is preferably provided which comprises at least one prosthesis with two bearing pieces, and one prosthesis with in each case one bearing piece. In this way, facet joints at two adjacent levels can be treated. However, further levels can also be added by additional use of prostheses with two bearing pieces. A particular advantage of the invention lies in this ability to provide treatment on multiple levels. With the prosthesis according to the invention, the natural biomechanics are substantially preserved, so that, even with use over several levels, the good biomechanical properties of the prosthesis according to the invention mean there is no danger of restricted mobility or of loss of stability.

The invention further relates to a method for implanting a prosthesis comprising a retaining piece and a bearing piece, wherein the bearing piece comprises a pressure plate and, lying opposite this, a bearing insert having an articular surface for interaction with an articular surface of an adjacent vertebra, said method involving steps in which a slit is excavated on the articular process of a vertebra so as to extend from one articular surface of the vertebra in the direction of the other articular surface of the vertebra, and the guide rod is inserted into the slit, with the bearing piece coming to rest with its pressure plate on the articular surface. The method according to the invention has the advantage that only a single slit has to be formed on the vertebra. This slit can be of small dimensions, since it only has to accommodate one guide element and is not exposed to retaining forces of the prosthesis. In particular, it is possible to form the slit in the dorsolateral direction. This permits a particularly good access and, consequently, a simplified operating technique. For implanting the prosthesis according to the invention with one bearing piece, it is not even necessary for the slit to extend through to the other articular surface; sufficient space for receiving the guide rod can often already be provided by a partial slit.

The introduction of the prosthesis from the side into the slit is easily achieved, and without great force being applied. For secure locking, it may be expedient that the guide rod has an oval cross section and, after introduction into the slit, is turned such that it wedges with its wide cross section in the slit. This permits easy insertion of the prosthesis according to the invention, and also good fixation of the prosthesis against inadvertent movement out of the slit. The slit can also be designed such that the guide rod has an overdimension. The dimensions are in this case chosen such that a press-fit between the guide rod and the slit is obtained.

BRIEF DESCRIPTION OF THE DRAWINGS

The invention is explained below with reference to the attached drawing in which advantageous illustrative embodiments are depicted, and in which:

FIGS. 1a), 1b) and c) show a side view, a front view and a rear view, respectively, of a first embodiment;

FIG. 2 shows a cross-sectional view along a line II-II from FIG. 1;

FIG. 3 shows an enlarged side view of an area of the cervical spine with implanted prosthesis according to a variant of the first embodiment;

FIGS. 4a) and 4b) show a partial longitudinal section and a transverse section, respectively, through a further variant of the first embodiment;

FIGS. 5a) and 5b) show a front view and a rear view, respectively, of a second embodiment of the prosthesis according to the invention;

FIG. 6 shows a partial view of the cervical spine with implanted cervical prosthesis according to the second embodiment;

DETAILED DESCRIPTION OF THE INVENTION

Figure 7:
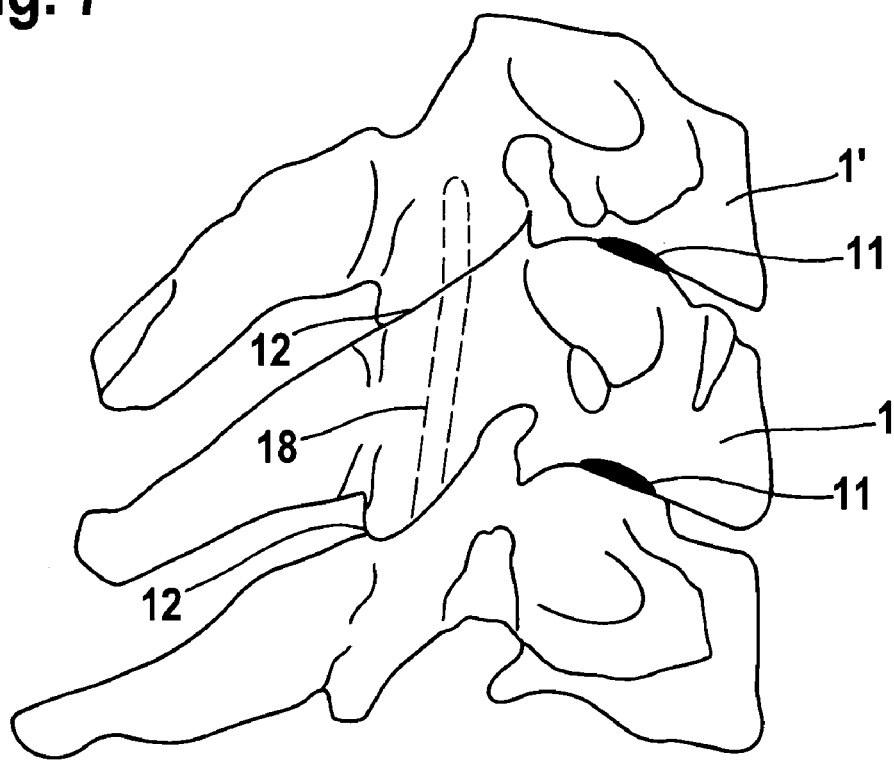
FIG. 7 shows a side view of an intended site of implantation on a cervical spine.

For better understanding of the invention, the intended site of implantation will first be explained. The prosthesis is provided for facet joints of the spinal column. FIG. 7 shows a detail of the human spinal column, more precisely a detail of the cervical spine. A plurality of vertebrae (three vertebrae) will be seen arranged above one another. In their anterior area (on the right of the drawing), the vertebrae comprise a medullary canal in which ascending and descending nerve bundles run. In their posterior area (on the left of the drawing), the vertebrae have a spinous process. On each of the sides of the vertebrae there is an articular process 15. The latter in each case has two articular surfaces, namely an upper articular surface 13 in the upper area, and a lower articular surface 14 in the lower area. The upper and lower articular surfaces 13, 14 of two vertebrae 1, 1' arranged one above the other interact with one another. They together form a facet joint 12. Vertebrae 1, 1' arranged above one another are in each case connected to one another via two facet joints 12 and an intervertebral disk 11.

Figure 8:
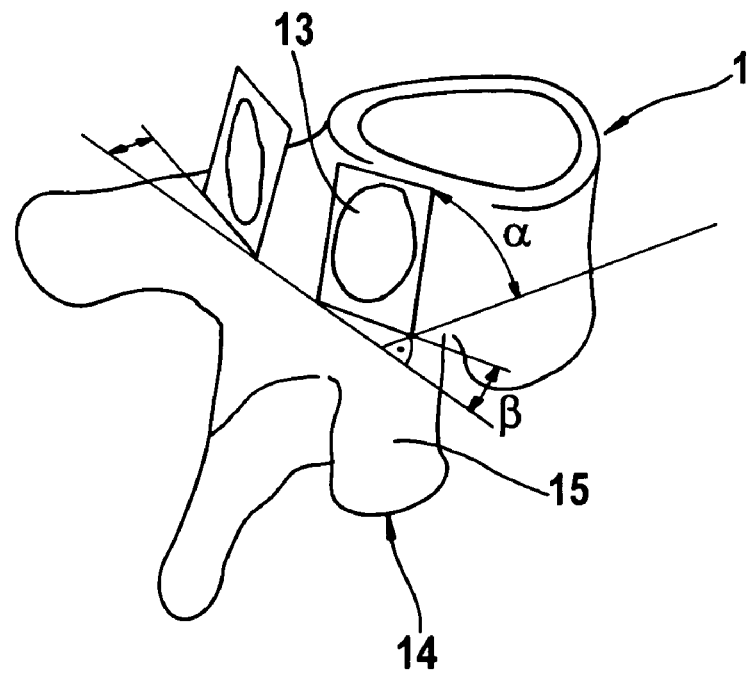
FIG. 8 shows an enlarged view of a cervical vertebra with explanatory details.

The upper articular surfaces 13 and their arrangement on the vertebra 1 are shown in more detail in FIG. 8. The upper articular surfaces 13 are located on the articular process 15. They are arranged, at a steep angle α of ca. 80° relative to the horizontal, on the posterior face of the vertebra 1. Moreover, the upper articular surfaces 13 are also turned outward by an angle relative to the transverse axis. This angle is shown as angle β in FIG. 8. It measures 20°, for example. The lower articular surface 14 is shaped correspondingly. It is arranged at the bottom on the articular process 15. The lower articular surface 14 of a vertebra 1' is designed in a manner matching the upper articular surface 13 of the vertebra 1 lying beneath it.

The invention envisages the replacement of articular surfaces 13, 14 that have become defective through disease or injury. A first embodiment of a prosthesis 2 according to the invention is depicted in FIGS. 1a)-c). The prosthesis comprises a guide rod 21 which is mounted on a bearing piece 23, so as to move between different angles, via a pivot hinge 22 designed as a pin bearing. The bearing piece 23 comprises a compression plate 24 on its side directed toward the guide rod 21, and, on its opposite side, it has a bearing shell 27. The latter can be made of a plastic material that promotes sliding (for example polyethylene). Provision can optionally be made for the bearing shell 27 to be made movable in rotation on the pressure plate 24. For this purpose, the pressure plate 24 has, on its top face, a pot-shaped recess into which the bearing shell 27 is mounted via a blunt underside. However, it is also possible for the bearing shell 27 to be made of a biocompatible metal alloy, for example CoCrNi. The latter opens up the favorable possibility of the bearing piece 23 with pressure plate 24 and bearing shell 27 being made in one piece. The face of the pressure plate 24 directed toward the guide rod 21 is designed to rest on the vertebra 1, more precisely on the articular surface 13, 14 that is to be treated. For better anchoring of the pressure plate 24 on the vertebra 1, projections are expediently provided which, in the embodiment shown, are designed as a circular toothing arrangement 25. In the implanted state, the toothing arrangement 25 engages in the articular surface 13, 14 to be treated, and it fixes the pressure plate 24 and, consequently, the bearing piece 23 of the prosthesis 2 according to the invention at the intended site.

The guide rod 21 is used to determine the position of the prosthesis 2. It is intended to form, on the articular process 15 of the vertebra 1, a slit 18 into the area of the facet joint 12 that is to be treated. This slit 18 is oriented in such a way that it extends through the articular process 15 in the direction from the upper articular surface 13 to the lower articular surface 14. The length of the slit 18 can extend along the full height of the articular process 15, or, as is shown in FIG. 3, an area adjacent to the articular surface 13, 14 to be treated. The cross section of the slit 18 can be dimensioned such that it is large enough to accommodate the guide rod 21 together with the pivot joint 22; in the case of a recessed arrangement of the pivot joint, it suffices for the cross section to be dimensioned to accommodate the guide rod 21. Such a variant, with a ball joint 22' as pivot joint on an integrally formed bearing piece 23, is shown in FIG. 4a. The prosthesis 2 according to the invention can be moved to its implantation site by simply inserting its guide rod 21 into the slit 18 on the articular process 15. By virtue of the pivot joint 22, the bearing piece 23 automatically orients itself such that it adopts an angle corresponding to the inclination α and β. The pressure plate 24 in this way comes to rest flat on the articular surface 13, 14 of the articular process 15 to be treated. The pressure plate 24 transmits bearing forces into the articular process 15. The guide rod 21 is basically only used for positioning the prosthesis 2, and does not have to transmit any bearing forces in the implanted state. Its dimensions can therefore be small. This makes it possible to correspondingly choose small dimensions for the slit 18. This in particular has the advantage that the smaller the width of the slit 18, the more likely it is to become rapidly closed after implantation. In this way, the prosthesis 2 is prevented, in a particularly reliable and biocompatible manner, from undesired dislocation from the slit 18.

To initially secure the prosthesis 2 to the greatest possible extent against slipping out of place after its implantation, the shaft of the guide rod 21 is preferably not cylindrical, but instead oval (FIG. 2) or rectangular (FIG. 4b). This makes it possible, at the time of implantation, to orient the guide rod 21 in such a way that it is pushed with its small cross section into the slit 18 (see broken line in FIG. 2). When the prosthesis 2 has been advanced to its intended implantation site in slit 18, its guide rod 21 is turned through 90°, such that the wide cross section of the guide rod 21 extends across the width of the slit 18. The width of the slit 18 is expediently chosen such that it is smaller than the greatest width of the oval-shaped guide rod 21. This means that, in the rotated position, a wedging effect is obtained which secures the guide rod 21 and therefore the prosthesis 2 at the implantation site. To further increase the safety of the attachment, the guide rod 21 can be provided with a serration 28 which, in the inserted state of the prosthesis 2, cuts into the bone substance surrounding the slit 18. A bracket 4 can also be provided for additional securing by means of a screw (not shown). It is also expedient if the pressure plate 24 and the guide rod 21 are coated with a coating that promotes growth, for example hydroxyapatite, at least on their surfaces intended to rest on the vertebra 1.

FIG. 3 shows a variant of the first embodiment in which a ball-shaped thickened part 29 is arranged on that end of the guide rod 21 remote from the bearing piece 23. It is received in a widened area 19 which is formed on the slit 18 at a distance from the articular surface corresponding to the length of the guide rod 21. This widened area can easily be produced by the surgeon during implantation, by means of a twist drill introduced from the side. By virtue of the rotationally symmetrical curvature of the ball-shaped thickened part 29 on its side directed toward the bearing piece 23, an almost planar, flush contact can be obtained, especially when the guide rod 21 is turned through 90 degrees for fixing it, as has been described above.

The bearing shell 27 can have a flat outer face as articular surface. However, it is preferable to give it a convex configuration (for the upper articular surface 13) or a concave configuration (for the lower articular surface 14), although a reverse configuration is also possible. The contour of the bearing piece 23 is expediently chosen such that the bearing shell 27 provided for replacement of the lower articular surface 14 has a rectangular envelope (for example the shape of a rectangle with rounded edges, see FIG. 1). By contrast, for treatment of the upper articular surface 13, the bearing shell preferably has a circular contour (see FIG. 5 and explanation hereinbelow).

A second embodiment of the invention is shown in FIGS. 5 and 6. Identical parts are provided with the same reference numbers. This second embodiment of the prosthesis 3 according to the invention mainly differs from the first embodiment 2 shown in FIGS. 1 and 2 in that a second bearing piece 33 is provided at the opposite end of the guide rod 21. The guide rod 21 is designed in two parts, with an additional inner guide rod 31. The distance of the upper bearing piece 23 from the lower bearing piece 33 can be altered by pushing the inner guide rod 31 in. Locking means 39 are preferably provided for securing purposes. It will be noted that alternative designs for length adjustment are also possible, for example by means of a screw thread 30 (see FIG. 5b). The lower bearing piece 33 is also connected to the guide rod 31 via a pivot joint so as to move between different angles. Said pivot joint is expediently designed as a cardan joint 32 movable in two rotational degrees of freedom.

To simplify the screwing-in procedure, a recess for a screwing tool is preferably provided on the outside of the bearing piece 33, namely of the bearing shell 37, in the embodiment shown in FIG. 5b. A hexagonal depression 38 is provided in the embodiment shown. It is preferably arranged such that it lies in the axial continuation of the inner guide rod 31. In this way, the inner guide rod 31 can easily be screwed into the guide rod 21 by means of a hexagon key, if appropriate after pivoting of the vertebra 1, 1' located above. If the access conditions are unfavorable, this can also be done with the lower bearing piece 33 at a slight inclination; greater angles are possible here if the pivot joint is designed as a cardan joint 32. In this way it is possible to exert pressure on the vertebra 1 via the bearing pieces 23, 33. Bone growth in the vertebra 1' can be stimulated in this way, with the result that the prosthesis 3 grows rapidly and safely into the vertebra 1'.

In FIG. 6, the second embodiment of the prosthesis 3 according to the invention is shown in the implanted state. It will be seen that the bearing piece 33 rests on the upper articular surface 13, and the bearing piece 23 rests on the lower articular surface 14 of the vertebra 1'. The prosthesis 3 is therefore suitable for treating the facet joints 12 lying at two consecutive levels. The adjacent vertebrae can be fitted with one prosthesis 2 provided with a bearing piece 23, or once again with prostheses 3 extending over two levels, or, if appropriate, they may not be fitted with any prosthesis. By virtue of the bearing piece 23, 33 and its bearing shells 27, 37 being configured in accordance with the physiological circumstances, it is possible for the prosthesis 2, 3 to interact via its bearing shell 37 with the natural articular surface 13, 14 of the adjacent vertebra 1. As is shown in FIG. 3, the bearing shell 27 interacts with the prosthesis 2 in the vertebra 1.

For implantation of the second embodiment of the prosthesis 3 according to the invention, the procedure is the same as for the first embodiment. However, the slit 18' is formed along the full height of the articular process 15.

An operating technique for the prosthesis according to the invention is explained below. This involves a posterior approach to the spinal column. An articular capsule (not shown) surrounding the facet joint 12 to be treated is exposed and opened. Since only a relatively small approach route is needed for implantation of the prosthesis 2, 3 according to the invention, it suffices for the articular capsule to be opened in a way in which it is damaged only to a minimum. It can also remain in place; in contrast to conventional operating techniques, removal of the articular capsule is not needed. On the contrary, after the prosthesis has been implanted, the capsule can be restored. The approach to the facet joint 12 is free after the articular capsule has been opened. In a subsequent step, a turbine reamer known per se is used to form a slit 18, 18' in the dorso-lateral direction on the articular process of the vertebrae 1, 1' into which the prostheses 2, 3 according to the invention is to be implanted. The slit 18, 18' extends in the direction from the upper articular surface 13 to the lower articular surface 14 of the respective articular process 15. The length of the slit 18, 18' can be chosen as required; for example, for implantation of the first embodiment of the prosthesis 2, on an area near the facet joint 12 in question, and, for implantation of the second embodiment 3, along the full height of the articular process 15. As has already been mentioned, the width of the slit 18, 18' can be chosen small, in order to promote rapid closure by bone growth. The prosthesis 2, 3 is then introduced with its guide rod 21, 31 into the slit 18, 18' and is pushed forward until the bearing pieces 23, 33 have reached the intended position on the articular surfaces 13, 14 of the facet joints 12 that are to be treated. If appropriate, the prosthesis 2, 3 is then fixed by rotating the oval or rectangular shaft 21. If required in the prosthesis according to the second embodiment 3, the length of the guide rod 21, 31 is varied until both bearing pieces 23, 33 rest with their respective pressure plates 24, 34 securely on the vertebrae. Implantation of the prosthesis 2, 3 is thus completed. After the surgical wound has been closed, initial stabilization of the prosthesis 2, 3 is achieved by turning the oval shaft 21, and, in the long term, the narrow width of the slit 18, 18' means that it can be expected to become closed by bone growth. This results in a lasting and biocompatible fixation of the prosthesis.

The invention claimed is:

1. A prosthesis for facet joints of the spinal column, comprising a first bearing piece, a retaining piece, a guide rod comprising an outer guide rod and an inner guide rod, and a locking device,
   the inner guide rod configured to engage in a telescopic manner with the outer guide rod, the locking device configured to secure the inner and outer guide rods against moving apart, and
   the first bearing piece comprising a first pressure plate configured to rest on a vertebra and, on a side opposite to the first pressure plate, a first bearing shell which has an articular surface configured to interact with an articular surface of a vertebra adjacent to the vertebra on which the first pressure plate rests,
   wherein a pivot joint is provided to secure the guide rod on the first bearing piece.

2. The prosthesis of claim 1, wherein the pivot joint is a cardan joint.

3. The prosthesis of claim 1, wherein a second bearing piece comprising a second pressure plate and a second bearing shell is arranged at another end of the guide rod.

4. The prosthesis of claim 3, wherein one of the first and second bearing pieces has a contour with an oval envelope, and the other of the first and second bearing pieces has a contour with a rectangular envelope.

5. The prosthesis of claim 3, wherein at least one of the first and second bearing pieces has a screw opening in its articular surface and is connected in a rotationally fixed manner to the inner guide rod.

6. The prosthesis of claim 3, wherein a thickened part is formed at the another end of the guide rod.

7. The prosthesis of claim 6, wherein the thickened part has a curvature on its side directed toward the first bearing piece.

8. The prosthesis of claim 7, wherein the curvature has a rotationally symmetrical design.

9. The prosthesis claim 6, 7 or 8, wherein the thickened part has a spheroid design.

10. The prosthesis of claim 3, wherein the second pressure plate is provided with a coating that promotes bone growth.

11. The prosthesis of claim 3, wherein the second bearing shell has an articular surface with a convex curvature.

12. The prosthesis of claim 1, wherein the first bearing piece comprising the first pressure plate and the first bearing shell are made in one piece.

13. The prosthesis of claim 1, wherein the guide rod is adapted for insertion into a slit between articular surfaces of the vertebra.

14. The prosthesis of claim 13, wherein the guide rod has a non-circular cross section whose greatest width is greater than the width of the slit.

15. The prosthesis of claim 14, wherein the interacting articular surface on the adjacent vertebra has a complementary curvature.

16. The prosthesis of claim 1 or 3, further comprising a radially protruding serration along the guide rod.

17. The prosthesis of claim 1, further comprising a toothing arrangement provided on the first pressure plate and adapted to engage in the vertebra.

18. The prosthesis of claim 1, wherein the first pressure plate is provided with a coating that promotes bone growth.

19. The prosthesis of claim 18, wherein the coating comprises hydroxyapatite.

20. The prosthesis of claim 1, wherein the first bearing shell has an articular surface with a convex curvature.

21. A prosthesis set comprising at least one prosthesis of claim 1 or 3, and including at least one prosthesis with two bearing pieces and at least one prosthesis with one bearing piece.

22. The prosthesis of claim 1, wherein the locking device comprises catch elements.

23. The prosthesis of claim 1, wherein the locking device comprises a self-locking screw connection.

* * * * *